United States Patent [19]

Morgan

[11] 4,450,155

[45] May 22, 1984

[54] ANALGESIC DIPEPTIDE AMIDES AND METHOD OF USE AND COMPOSITIONS THEREOF

[75] Inventor: Barry A. Morgan, Albany, N.Y.

[73] Assignee: Sterling Drug Inc., New York, N.Y.

[21] Appl. No.: 423,054

[22] Filed: Sep. 24, 1982

Related U.S. Application Data

[63] Continuation-in-part of Ser. No. 286,672, Jul. 24, 1981, abandoned.

[51] Int. Cl.$^3$ ................. A61K 37/00; C07C 103/52
[52] U.S. Cl. ..................... 424/177; 260/112.5 E; 260/112.5 R
[58] Field of Search ................. 260/112.5 E, 112.5 R; 424/177

[56] References Cited

U.S. PATENT DOCUMENTS

| | | | |
|---|---|---|---|
| 4,127,535 | 11/1978 | Coy et al. | 260/112.5 R |
| 4,178,371 | 12/1979 | Morgan | 260/112.5 E |
| 4,261,883 | 4/1981 | Smolarsky | 260/112.5 E |
| 4,350,627 | 9/1982 | de Castiglione et al. | 260/112.5 E |
| 4,380,535 | 4/1983 | Sarantakis | 260/112.5 E |

OTHER PUBLICATIONS

McGregor et al., Life Sciences, vol. 23, No. 13, pp. 1371–1376, 1978.

Roques et al., European Journal of Pharmacology, vol. 60, pp. 109–110, 1979.

*Primary Examiner*—Delbert R. Phillips
*Attorney, Agent, or Firm*—Theodore C. Miller; Paul E. Dupont; B. Woodrow Wyatt

[57] ABSTRACT

A genus of dipeptide amides including as the preferred subgenus the dipeptide amides having the structural formula $R_1TyrProNR_4R_5$ wherein $R_1$ is hydrogen or alkyl, $R_4$ is phenylalkyl or substituted-phenylalkyl and $R_5$ is hydrogen, alkyl, phenylalkyl or substituted-phenylalkyl are prepared by condensing the dipeptide with the amine or the amino acid with the amino acid amide and are useful as analgesics.

13 Claims, No Drawings

ANALGESIC DIPEPTIDE AMIDES AND METHOD OF USE AND COMPOSITIONS THEREOF

CROSS-REFERENCE TO RELATED APPLICATION

This application is a continuation-in-part of my copending application Ser. No. 286,672 filed July 24, 1981 and now abandoned.

BACKGROUND OF THE INVENTION

1. Field of the Invention

The invention relates to dipeptide amides which are useful as analgesics.

2. Description of the Prior Art

Coy and Kastin U.S. Pat. No. 4,127,535 describes

H-Tyr-X-Y wherein: X is a chiral residue of a D-amino acid selected from the group consisting of D-alanine, D-leucine, D-isoleucine, D-valine, D-phenylalanine, D-tyrosine, D-trytophan, D-serine, D-threonine, D-methionine, D-glutamic acid, D-glutamine, D-proline[,] D-aspartic acid, D-asparagine, D-lysine, D-arginine and D-histidine; and Y is selected from the group consisting of hydroxy, amino, loweralkylamino, diloweralkylamino and lower alkoxy which are stated to be useful as analgesic, tranquilizer, sedative, hypnotic, anti-depressant[,] prolactin releasing and growth hormone releasing agents and which are designated in the illustrative examples as derivatives of β-lipotropin fragment 61-62. Example 34 specifically describes D-Ala$^2$-β-lipotropin fragment 61-62 amide by name and method of preparation but does not describe any chemical or biological properties thereof.

McGregor (et al., Life Sciences, vol. 23, no. 13, pp. 1371-1378, 1978) describes H-Tyr-D-Ala-NH$_2$ (D-Ala$^2$-β-lipotropin fragment 61-62 amide) and shows that it is greater than 10 times less potent intravenously and 200 times less potent intraventricularly in the tail flick test for analgesia in the rat, and binds to the opiate receptor in rat brain membranes with 830 times less affinity, than morphine.

Roques (et al., European Journal of Pharmacology, vol. 60, pp. 109-110, 1979) describes HTyrD-AlaNH(CH$_2$)$_2$NH(CH$_2$)$_2$Phenyl, which was less then 1% as potent as Met-enkephalin in both the guinea pig ileum and mouse vas deferens tests.

SUMMARY OF THE INVENTION

In a composition of matter aspect the invention is 2-(L-N$^2$-R$_1$-N-R$_2$-tyrosylamino)-2-R$_3$-N-R$_4$-N-R$_5$-acetamide having the structural formula

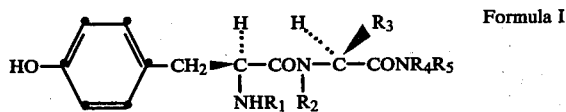

Formula I wherein

R$_1$ is hydrogen, alkyl of one to five carbon atoms, allyl, cyclopropylmethyl, formyl, acetyl or propionyl;

R$_2$ taken together with R$_3$ is dimethylene, trimethylene or tetramethylene;

R$_4$ is (CH$_2$)$_n$Y, wherein n is an integer from 2 through 10 and Y is phenyl or phenyl substituted by fluoro, chloro, methyl or methoxy; and R$_5$ is hydrogen, alkyl of one to five carbon atoms or (CH$_2$)$_n$Y as defined for R$_4$;

or a pharmaceutically acceptable acid addition salt thereof.

The compounds of Formula I are useful as analgesics.

In a first process aspect the invention is the process of preparing 2-(L-N$^2$-R$_1$-N-R$_2$-tyrosylamino)-2-R$_3$-N-R$_4$-N-R$_5$-acetamide of Forumula I which comprises condensing the corresponding L-N-R$_1$-tyrosine with the corresponding 2-R$_2$NH-2-R$_3$-acetic acid to form the corresponding 2-(L-N$^2$-R$_1$-N-R$_2$-tyrosylamino)-2-R$_3$-acetic acid and then condensing said 2-(L-N$^2$-R$_1$-N-R$_2$-tyrosylamino)-2-R$_3$-acetic acid with the corresponding HNR$_4$R$_5$, concomitantly protecting and deprotecting the α-amino, tyrosyl phenolic hydroxyl and acetyl carboxyl groups as required.

In a second process aspect the invention is the process of preparing 2-(L-N$^2$-R$_1$-N-R$_2$-tyrosylamino)-2-R$_3$-N-R$_4$-N-R$_5$-acetamide of Formula I which comprises condensing the corresponding L-N-R$_1$-tyrosine with the corresponding 2-R$_2$NH-2-R$_3$-acetic acid methyl ester to form the corresponding 2-(L-N$^2$-R$_1$-N-R$_2$-tyrosylamino)-2-R$_3$-acetic acid methyl ester, then condensing said 2-(L-N$^2$-R$_1$-N-R$_2$-tyrosylamino)-2-R$_3$-acetic acid methyl ester with hydrazine to form 2-(L-N$^2$-R$_1$-N-R$_2$-tyrosylamino)-2-R$_3$-acetyl hydrazide, then reacting said 2-(L-N$^2$-R$_1$-N-R$_2$-tyrosylamino)-2-R$_3$-acetyl hydrazide with an alkyl nitrite to form 2-(L-N$^2$-R$_1$-N-R$_2$-tyrosylamino)-2-R$_3$-acetyl azide, then condensing said 2-(L-N$^2$-R$_1$-N-R$_2$-tyrosylamino)-2-R$_3$-acetyl azide with the corresponding HNR$_4$R$_5$, concomitantly protecting and deprotecting the α-amino and tyrosyl phenolic hydroxyl groups as required.

In a third process aspect the invention is the process of preparing 2-(L-N$^2$-R$_1$-N-R$_2$-tyrosylamino)-2-R$_3$-N-R$_4$-N-R$_5$-acetamide of Formula I which comprises condensing the corresponding 2-R$_2$NH-2-R$_3$-acetic acid with the corresponding HNR$_4$R$_5$ to form the corresponding 2-R$_2$NH-2-R$_3$-N-R$_4$-N-R$_5$-acetamide and then condensing said 2-R$_2$NH-2-R$_3$-N-R$_4$-N-R$_5$-acetamide with L-N-R$_1$-tyrosine, concomitantly protecting and deprotecting the α-amino and tyrosyl phenolic hydroxyl groups as required.

In a method of use aspect the invention is the method of producing analgesia in a mammal in pain which comprises administering to the mammal an analgesically effective amount of 2-(L-N$^2$-R$_1$-N-R$_2$-tyrosylamino)-2-R$_3$-N-R$_4$-N-R$_5$-acetamide of Formula I or a pharmaceutically acceptable acid addition salt thereof.

In another composition of matter aspect the invention is a pharmaceutical composition for producing analgesia in a mammal consisting essentially of 2-(L-N$^2$-R$_1$-N-R$_2$-tyrosylamino)-2-R$_3$-N-R$_4$-N-R$_5$-acetamide of Formula I or a pharmaceutically acceptable acid addition salt thereof and a pharmaceutically acceptable vehicle.

When R$_1$ or R$_5$ of Formula I is alkyl of one to five carbon atoms, it can be any of the possible primary, secondary and tertiary alkyls of one to five carbon atoms, especially including methyl, ethyl, n-propyl, isopropyl, n-butyl, tert-butyl, n-pentyl and 3-methylbutyl.

In a preferred composition of matter aspect the invention is N-R$_1$-L-tyrosyl-N-R$_4$-N-R$_5$-L-prolinamide having the structural formula

  Formula II, which is the compound of Formula I wherein R$_2$ and R$_3$ taken together are trimethylene, or a pharmaceutically acceptable acid addition salt thereof.

In a most preferred composition of matter aspect the invention is the following compounds of Formula II, which are the free base forms of the examples whose preparation and biological properties are described below.

| Compound of Formula II | Example |
|---|---|
| HTyrProNH(CH$_2$)$_2$Ph | 1 |
| HTyrProNH(CH$_2$)$_3$Ph | 2 |
| HTyrProNMe(CH$_2$)$_3$Ph | 3 |

In Formula II and the foregoing formulas of specific compounds of Formula II
Tyr represents L-tyrosyl,
Pro represents L-prolyl,
Me represents methyl, and
Ph represents phenyl.
The symbols Tyr and Pro do not include the N-terminal and C-terminal groups. H of HTyr or Me of MeTyr is the same as R$_1$ of Formula I when R$_1$ is hydrogen or methyl, H of NH or Me of NMe is the same as R$_5$ of Formula I when R$_5$ is hydrogen or methyl, and R$_1$, R$_4$ and R$_5$ are otherwise the same as R$_1$, R$_4$ and R$_5$ of Formula I.

DETAILED DESCRIPTION OF THE INVENTION INCLUSIVE OF THE PREFERRED EMBODIMENTS

Preparation of the Compounds

The protection, activation, condensation and deprotection steps required to prepare the compounds of Formula I are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid and dipeptide intermediates can be formed and used with or without being isolated and include the acyl halides and pseudohalides, especially the acyl azides; the anhydrides, especially the mixed anhydrides and most especially the mixed anhydride with diphenylphosphinyl chloride, isobutyl chloroformate or pivalyl chloride; derivatives formed by addition reactions, especially using dicyclohexylcarbodimide; displaceable acyl derivatives of heterocyclic nitrogen; ring-openable activated heterocyclic systems; acylphosphonium derivatives; activated esters, especially N-hydroxysuccinimide, nitrophenyl and pentafluorophenyl esters; and polymeric (solid phase) derivatives.

It is necessary that the N-terminal α-amino function be protected during the amide forming steps. It is preferred but not essential that the tyrosyl phenolic hydroxyl also be protected. The preferred α-amino protecting groups are benzyloxycarbonyl (Z), which can be removed by catalytic hydrogenation using palladium as catalyst or by hydrogen bromide in acetic acid, and tert-butyloxycarbonyl (Boc), which can be removed by acidic cleavage, for example, with hydrogen chloride in a suitable solvent or trifluoroacetic acid. Benzyl (Bz) and tert-butyl (tBu) are the preferred tyrosyl phenolic hydroxyl protecting groups. Benzyl can be removed by catalytic hydrogenation using palladium as catalyst or by hydrogen bromide in acetic acid. tert-Butyl can be removed by acidic cleavage, for example, with hydrogen chloride in a suitable solvent or trifluoroacetic acid.

The C-terminal carboxyl group must be protected during the peptide forming step. In the first process aspect it is protected as the amide, which is, of course, not removed. In the second process aspect the methyl ester protects the carboxyl group during peptide bond formation and subsequently activates it for hydrazide bond formation. In the third process aspect the C-terminal carboxyl group can be protected as the carboxylate salt, the t-butyl ester, which can be removed by acidic cleavage, for example, with hydrogen chloride in a suitable solvent or trifluoroacetic acid, or the benzyl ester, which can be removed by catalytic hydrogenation using palladium as catalyst.

The unprotected and protected L-N-R$_1$-tyrosine, unprotected and protected 2-R$_2$NH-2-R$_3$-acetic acid, 2-R$_2$NH-2-R$_3$-acetic acid methyl ester and HNR$_4$R$_5$ starting materials are known classes of compounds. The individual compounds are commercially available or can be made by methods specifically or generally described in the chemical literature.

The acid addition salts of the compounds of Formula I are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The compounds of Formula I and the acid addition salts thereof are hydrophilic and may form solvates with water or hydrophilic organic solvents or mixtures thereof. If the resulting products are crystalline, they are purified by recrystallization. If they are non-crystalline, which is generally so, they are purified by high pressure liquid chromatography or column chromatography and/or isolated by lyophylization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GLC), high pressure liquid chromatography (HPLC), thin layer chromatography (TLC) and/or amino acid analysis.

EXAMPLE 1

HTyrProNH(CH$_2$)$_2$Ph

A. BocProNH(CH$_2$)$_2$Ph

Triethylamine (2.8 ml.) was added with stirring to a solution of N-(tert-butyloxycarbonyl)-L-proline (4.3 g.) in tetrahydrofuran (50 ml.) maintained at 0° C. The temperature was lowered to −20° C., isobutyl chloroformate (2.7 ml.) was added, and stirring was continued for 15 minutes. 2-Phenylethylamine (2.5 ml.) was then added with continued stirring, and the mixture was allowed to warm to room temperature and filtered. Concentration of the filtrate afforded a solid. Crystallization of the solid from ethyl acetate gave the product in two parts by filtration and in a third part from the filtrate, which was washed with water, aqueous citric acid (5%), saturated aqueous sodium chloride and saturated aqueous sodium bicarbonate, then dried and concentrated. High pressure liquid chromatography of the three parts on silica gel (350 g.) using hexane-ethyl acetate (7:3) as the eluant (200 ml./min.) afforded in fractions 7-8 1-(tert-butyloxycarbonyl)-N-(2-phenylethyl)-L-prolinamide (3.2 g., m.r. 153°-154° C.)

B. HProNH(CH$_2$)$_2$Ph

A solution of 1-(tert-butyloxycarbonyl)-N-(2-phenylethyl)-L-prolinamide (2.46 g.) in ethyl acetate-hydrogen chloride (3.9 N, 30 ml.) was stirred for 20 minutes at room temperature, then diluted with ether (to about 200 ml.). The solvents were decanted from the resulting gum, which was triturated with ether, affording crystalline N-(2-phenylethyl)-L-prolinamide hydrochloride (1.91 g., m.r. 147°-150° ).

C. ZTyr(Bz)ProNH(CH$_2$)$_2$Ph

Triethylamine (0.84 ml.) was added to a solution of N-benzyloxycarbonyl-O-benzyl-L-tyrosine succinimidate ester (prepared from N-benzyloxycarbonyl-O-benzyl-L-tyrosine, N-hydroxysuccinimide and dicyclohexylcarbodiimide; 3.02 g.), N-(2-phenylethyl)-L-prolinamide hydrochloride (1.53 g.) and dimethylformamide (20 ml.) The solution was stirred at room temperature for three hours, then concentrated under vacuum (0.05 mm. of mercury). An ethyl acetate solution of the residue was washed with water, aqueous citric acid (5%), saturated aqueous sodium chloride and saturated aqueous sodium becarbonate, dried and concentrated. High pressure liquid chromatography of the resulting syrup (3.27 g.) on silica gel (350 g.) using hexane-ethyl acetate (1:1) as the eluant (200 ml./min.) afforded in fractions 7-9 (N-benzyloxycarbonyl-O-benzyl-L-tyrosyl)-N-(2-phenylethyl)-L-prolinamide (2.78 g.).

D. HTyrProNH(CH$_2$)$_2$Ph

A mixture of (N-benzyloxycarbonyl-O-benzyl-L-tyrosyl)-N-(2-phenylethyl)-L-prolinamide (2.5 g.), palladium on carbon (10%, 0.4 g.) and acetic acid (total volume 50 ml.) was hydrogenated at room temperature under pressure (40-50 p.s.i.g., uptake 80% at 6 hr.). The mixture was filtered and the filtrate was concentrated under vacuum (0.05 mm. of mercury). Water was added to the residue, the solution was concentrated, and these two steps were repeated. An aqueous solution of the residue was filtered and lyophilized. C, H and N elemental analysis of the residue were not in accord with the values calculated for the monoacetate salt monohydrate of the desired product. Purification of the residue by reverse phase high pressure liquid chromatography on octadecylsilated silica gel (350 g.) using ammonium acetate (0.15%) in methanol-water (55:45) as the eluant (100 ml./min.) gave in fraction 3 ($k^1$=2.2-3.4) a product, which was passed through the column again. Elution was first with water to remove ammonium acetate and then with methanol to remove the product, which was converted into the phosphate salt on the ion exchange column and lyophilized, affording L-tyrosyl-N-(2-phenylethyl)-L-prolinamide phosphate salt (1:1) sesquihydrate, whose free base is the compound of Formula II wherein R$_1$ and R$_5$ are each hydrogen and R$_4$ is (CH$_2$)$_n$Y wherein n is 2 and Y is phenyl.

EXAMPLE 2

HTyrProNH(CH$_2$)$_3$Ph

A. BocProNH(CH$_2$)$_3$Ph

By the method of part A of Example 1 N-(tert-butyloxycarbonyl)-L-proline (4.3 g.) was condensed with 3-phenylpropylamine (2.7 g.) and the product was purified by high pressure liquid chromatography on silica gel using hexaneethyl acetate (7:3) as the eluant, affording 1-(tert-butyloxycarbonyl)-N-(3-phenylpropyl)-L-prolinamide (3.48 g.).

B. HProNH(CH$_2$)$_3$Ph

A solution of 1-(tert-butyloxycarbonyl)-N-(3-phenylpropyl)-L-prolinamide (2.88 g.) in ethyl acetate-hydrogen chloride (3.9 N, 30 ml.) was stirred at room temperature for one half hour, then concentrated. A solution of the residue (2.80 g.) in ethyl acetate was concentrated, affording N-(3-phenylpropyl)-L-prolinamide hydrochloride as a syrup.

C. ZTyr(Bz)ProNH(CH$_2$)$_3$Ph

By the method of part C of Example 1 N-benzyloxycarbonyl-O-benzyl-L-tyrosine succinimidate ester (3.2 g.) was condensed with N-(3-phenylpropyl)-L-prolinamide hydrochloride (1.71 g.) and the product was purified by high pressure liquid chromatography on silica gel using ethyl acetate-hexane (3:2) as the eluant, affording (N-benzyloxycarbonyl-O-benzyl-L-tyrosyl)-N-(3-phenylpropyl)-L-prolinamide as a viscous syrup (2.22 g.).

D. HTyrProNH(CH$_2$)$_3$Ph

By the method of part D of Example 1 (N-benzyloxycarbonyl-O-benzyl-L-tyrosyl)-N-(3-phenylpropyl)-L-prolinamide (2.16 g.) was deprotected, the product was purified by reverse phase high liquid chromatography on octadecylsilated silica gel using ammonium acetate (0.15%) in methanol-water (58:42) as the eluant, and a solution thereof (1.1 g.) in dilute hydrochloric acid (0.0936 N, 27 ml.) and water (10 ml.) was lyophilized, affording as an amorphous white solid L-tyrosyl-N-(3-phenylpropyl)-L-prolinamide monohydrochloride sesquihydrate (649 mg.; $[\alpha]_D^{25}$ −14.8°, c=1, methanol), whose free base is the compound of Formula II wherein R$_1$ and R$_5$ are each hydrogen and R$_4$ is (CH$_2$)$_n$Y wherein n is 3 and Y is phenyl.

EXAMPLE 3

HTyrProNMe(CH$_2$)$_3$Ph

A. BocProNMe(CH$_2$)$_3$Ph

By the method of part A of Example 1 N-(tert-butyloxycarbonyl)-L-proline (4.3 g.) was condensed with N-methyl-3-phenylpropylamine hydrochloride (3.71 g.) and the product was purified by high pressure liquid chromatography on silica gel using hexane-ethyl acetate (3:2) as the eluant, affording 1-(tert-butyloxycarbonyl)-N-methyl-N-(3-phenylpropyl)-L-prolinamide as a syrup (2.65 g.).

B. HProNMe(CH$_2$)$_3$Ph

A solution of 1-(tert-butyloxycarbonyl)-N-methyl-N-(3-phenylpropyl)-L-prolinamide in ethyl acetate-hydrogen chloride (3,9 N, 30 ml.) was stirred at room temperature for one hour, then concentrated, affording N-methyl-N-(3-phenylpropyl)-L-prolinamide hydrochloride as a syrup (2.4 g.).

C. ZTyr(Bz)ProNMe(CH$_2$)$_3$Ph

By the method of part C of Example 1 N-benzyloxycarbonyl-O-benzyl-L-tyrosine succinimidate ester (3.5 g.) was condensed with N-methyl-N-(3-phenylpropyl)-

L-prolinamide hydrochloride (2.24 g.) and the product (2.84 g.) after filtration through silica gel was purified by high pressure liquid chromatography on silica gel using ethyl acetate-hexane (3:2) as the eluant, affording (N-benzyloxycarbonyl-O-benzyl-L-tyrosyl)-N-methyl-N-(3-phenylpropyl)-L-prolinamide.

D. HTyrProNMe(CH$_2$)$_3$Ph

By the method of part D of Example 1 (N-benzyloxycarbonyl-O-benzyl-L-tyrosyl)-N-methyl-N-(3-phenylpropyl)-L-prolinamide (2.4 g.) was deprotected, the product was purified by reverse phase high pressure liquid chromatography on octadecylated silica gel using ammonium acetate (0.15%) in methanol-water (3:2) as the eluant, and a solution thereof in dilute hydrochloric acid (0.0936N, 50 ml.) was lyophilized. Relyophilization of the product (707 mg.) afforded as an amorphous white solid L-tyrosyl-N-methyl-N-(3-phenylpropyl)-L-prolinamide monohydrochloride (570 mg., $[\alpha]_D^{25} -13.7°$. c=1, methanol), whose free base is the compound of Formula II wherein R$_1$ is hydrogen, R$_4$ is (CH$_2$)$_n$Y wherein n is 3 and Y is phenyl and R$_5$ is methyl.

BIOLOGICAL PROPERTIES OF THE COMPOUNDS

As stated above the compounds of Formula I are useful as analgesic agents. This utility has been shown by the results of testing the examples in vitro in the guinea pig ileum test.

Guinea Pig Ileum Test

Adult male guinea pigs (Charles River, Hartley strain) weighing 300-500 g. are decapitated, and the terminal ileum is exposed by reflecting the overlying cecum, severed at the ileocecal juncture, and removed while cutting the mesenteric attachments to avoid excessive traction on the tissue. The ileum (about 30 cm. in length) is transferred to a beaker containing warm modified Krebs-Henseleit solution (118 mM sodium chloride, 4.75 mM potassium chloride, 2.54 mM calcium chloride, 1.19 mM potassium dihydrogen phosphate, 1.2 mM magnesium sulfate, 25 mM sodium bicarbonate, 11 mM glucose, 20 $\mu$M choline chloride and 0.125 $\mu$M pyrilamine maleate). The terminal (aboral) portion (about 10 cm. in length) is discarded, and segments (3-4 cm. in length) are cut from the remainder and gently slid onto a glass rod (5-6 mm. in diameter) and arranged so that the mesenteric attachment is in a straight line. A cotton swab moistened in the solution is then carefully used to separate the longitudinal muscle from the underlying circular muscle. The longitudinal muscle and adhering myenteric plexus is then gently removed from the remaining tissue with forceps.

Strips of this prepared longitudinal muscle are mounted in a double-jacketed organ bath (5 ml.) under tension (1.0 g.), connected to isometric transducers (Grass FT .03), bathed in the modified Krebs-Henseleit solution described above, aerated with oxygen-carbon dioxide (95:5) and maintained at 37° C.

Stimulators (Grass S-44) are set to deliver repetitive monophasic square wave field stimulation (supramaximal voltage, 0.10 Hz., 0.25 msec. duration) through platinum ring electrodes at the top and bottom of the bath. Regular contractions of the muscle, which result from electrically-induced liberation of acetylcholine from postganglionic parasympathetic nerves, are recorded on a polygraph (Grass model 5). Following tissue equilibration (45-60 min.) and repeated washing (every 10 min.) an aqueous solution of a reference or test compound is added to the bath in a microliter volume (1.25-250 $\mu$l) and reductions in muscle twitch height are recorded. More compound can be added with (single dose method) or without (cumulative dose method) first washing the preparation.

From the results a half-maximal inhibitory concentration (IC50) value for the compound is computed by regression analysis of a linear plot of logarithm of concentration against percent of inhibition of twitch height (probits). The ratio of the IC50 value of a reference compound to that of a test compound tested in the same preparation is the molar potency ratio. Usually four preparations are tested simultaneously by the same person (N=4), and the resulting four molar potency ratios are averaged.

The following results were obtained using the examples as test compounds and Met$^5$-enkephalin as the reference compound:

| Compound | Average Molar Potency Ratio |
| --- | --- |
| Met$^5$—enkephalin | 100 |
| Example 1 | 117 |
| Example 2 | 6 |
| Example 3 | 9 |

To carry out the method of use and pharmaceutical composition aspects of the invention the compounds of Forumula I can be administered orally or parenterally in liquid or solid dosage form as solutions, suspensions, emulsions, capsules or tablets, which are prepared with conventional pharmaceutical vehicles and adjuncts by conventional pharmaceutical techniques.

I claim:

1. 2-(L-N$^2$-R$_1$-N-R$_2$-tyrosylamino)-2-R$_3$-N-R$_4$-N-R$_5$-acetamide having the structural formula

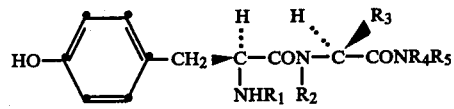

wherein
R$_1$ is hydrogen, alkyl of one to five carbon atoms, allyl, cyclopropylmethyl, formyl, acetyl or propionyl;
R$_2$ taken together with R$_3$ is dimethylene, trimethylene or tetramethylene;
R$_4$ is (CH$_2$)$_n$Y, wherein n is an integer from 2 through 10 and Y is phenyl or phenyl substituted by fluoro, chloro, methyl or methoxy; and
R$_5$ is hydrogen, alkyl of one to five carbon atoms or (CH$_2$)$_n$Y as defined for R$_4$;
or a pharmaceutically acceptable acid addition salt thereof.

2. A compound according to claim 1 wherein R$_2$ and R$_3$ taken together are trimethylene and having the structural formula

or a pharmaceutically acceptable acid addition salt thereof.

3. A compound according to claim 2 wherein R$_1$ is hydrogen or a pharmaceutically acceptable acid addition salt thereof.

4. A compound according to claim 2 wherein $R_4$ is $(CH_2)_nY$ wherein Y is phenyl or a pharmaceutically acceptable acid addition salt thereof.

5. A compound according to claim 4 wherein $R_5$ is hydrogen or a pharmaceutically acceptable acid addition salt thereof.

6. The compound according to claim 5 wherein n is 2 or a pharmaceutically acceptable acid addition salt thereof.

7. L-Tyrosyl-N-(2-phenylethyl)-L-prolinamide phosphate (1:1) salt sesquihydrate according to claim 6.

8. The compound according to claim 5 wherein n is 3 or a pharmaceutically acceptable acid addition salt thereof.

9. L-Tyrosyl-N-(3-phenylpropyl)-L-prolinamide monohydrochloride sesquihydrate according to claim 8.

10. A compound according to claim 4 wherein $R_5$ is methyl or a pharmaceutically acceptable acid addition salt thereof.

11. The compound according to claim 10 wherein N is 3 or a pharmaceutically acceptable acid addition salt thereof.

12. L-Tyrosyl-N-methyl-N-(3-phenylpropyl)-L-prolinamide monohydrochloride according to claim 11.

13. A pharmaceutical composition for producing analgesia in a mammal consisting essentially of 2-(L-$N^2$-$R_1$-N-$R_2$-tyrosylamino)-2-$R_3$-N-$R_4$-N-$R_5$-acetamide according to claim 1 or a pharmaceutically acceptable acid addition salt thereof and a pharmaceutically acceptable vehicle.

* * * * *

UNITED STATES PATENT AND TRADEMARK OFFICE
CERTIFICATE OF CORRECTION

PATENT NO. : 4,450,155
DATED : May 22, 1984
INVENTOR(S) : Barry A. Morgan

It is certified that error appears in the above-identified patent and that said Letters Patent is hereby corrected as shown below:

Cover page, item [75], "Albany" should read -- Colonie --.

Column 10 after claim 13, add claim 14 as follows:

14. The method of producing analgesia in a mammal in pain which comprises administering to the mammal an analgesically effective amount of 2-(L-$N^2$-$R_1$-N-$R_2$-tyrosylamino)-2-$R_3$-N-$R_4$-N-$R_5$-acetamide according to claim 1 or a pharmaceutically acceptable acid addition salt thereof.

On the title page "13 Claims, No Drawings" should read -- 14 Claims, No Drawings--.

Signed and Sealed this

Second Day of April 1985

[SEAL]

Attest:

DONALD J. QUIGG

*Attesting Officer*  *Acting Commissioner of Patents and Trademarks*